US010457911B2

(12) United States Patent
Kuriyama et al.

(10) Patent No.: US 10,457,911 B2
(45) Date of Patent: Oct. 29, 2019

(54) MEDIUM FOR STEM CELL USE

(71) Applicant: AJINOMOTO CO., INC., Tokyo (JP)

(72) Inventors: Yoko Kuriyama, Kawasaki (JP);
Satoru Okamoto, Kawasaki (JP);
Manabu Kitazawa, Kawasaki (JP);
Nao Sugimoto, Kawasaki (JP); Takuya Matsumoto, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 23 days.

(21) Appl. No.: 15/275,586

(22) Filed: Sep. 26, 2016

(65) Prior Publication Data

US 2017/0009200 A1 Jan. 12, 2017

Related U.S. Application Data

(63) Continuation of application No. PCT/JP2014/071256, filed on Aug. 12, 2014.

(30) Foreign Application Priority Data

Mar. 31, 2014 (JP) ................................. 2014-070763

(51) Int. Cl.
C12N 5/00 (2006.01)
C12N 5/074 (2010.01)

(52) U.S. Cl.
CPC ......... *C12N 5/0018* (2013.01); *C12N 5/0696* (2013.01); *C12N 2500/50* (2013.01); *C12N 2501/998* (2013.01)

(58) Field of Classification Search
CPC .................. C12N 5/0018; C12N 5/0696
See application file for complete search history.

(56) References Cited

U.S. PATENT DOCUMENTS

| 8,048,999 | B2 | 11/2011 | Yamanaka et al. |
| 8,058,065 | B2 | 11/2011 | Yamanaka et al. |
| 8,129,187 | B2 | 3/2012 | Yamanaka et al. |
| 8,153,429 | B2 | 4/2012 | Robins et al. |
| 8,211,699 | B2 | 7/2012 | Robins et al. |
| 8,278,104 | B2 | 10/2012 | Yamanaka et al. |
| 8,415,158 | B2 | 4/2013 | Robins et al. |
| 8,658,352 | B2 | 2/2014 | Robins et al. |
| 8,685,726 | B2 | 4/2014 | Schulz et al. |
| 9,365,830 | B2 | 6/2016 | Schulz et al. |
| 9,458,426 | B2 | 10/2016 | Schulz et al. |
| 2004/0087021 | A1 | 5/2004 | Heron |
| 2008/0113433 | A1 | 5/2008 | Robins et al. |
| 2008/0268534 | A1 | 10/2008 | Robins et al. |
| 2009/0047263 | A1 | 2/2009 | Yamanaka et al. |
| 2009/0068742 | A1 | 3/2009 | Yamanaka |
| 2009/0227032 | A1 | 9/2009 | Yamanaka et al. |
| 2010/0034785 | A1 | 2/2010 | Pedersen et al. |
| 2010/0062533 | A1 | 3/2010 | Yamanaka |
| 2010/0210014 | A1 | 8/2010 | Yamanaka |
| 2010/0216236 | A1 | 8/2010 | Yamanaka |
| 2010/0317104 | A1 | 12/2010 | Elefanty et al. |
| 2012/0021513 | A1 | 1/2012 | Schulz et al. |
| 2012/0214237 | A1 | 8/2012 | Robins et al. |
| 2013/0059386 | A1 | 3/2013 | Yamanaka et al. |
| 2013/0136721 | A1 | 5/2013 | Zambidis et al. |
| 2013/0280802 | A1 | 10/2013 | Schulz et al. |
| 2013/0309708 | A1 | 11/2013 | Robins et al. |
| 2014/0154802 | A1 | 6/2014 | Robins et al. |
| 2014/0186948 | A1 | 7/2014 | Schulz et al. |
| 2016/0145569 | A1 | 5/2016 | Robins et al. |
| 2016/0281058 | A1 | 9/2016 | Schulz et al. |

FOREIGN PATENT DOCUMENTS

| JP | 2004-135672 A | 5/2004 |
| JP | 2007-228815 A | 9/2007 |
| WO | WO 2007/069666 A1 | 6/2007 |
| WO | WO 2007/101130 A2 | 9/2007 |
| WO | WO 2008/056166 A2 | 5/2008 |
| WO | WO 2010/129294 A2 | 11/2010 |
| WO | WO 2011/100286 A2 | 8/2011 |
| WO | WO 2012/078153 A1 | 6/2012 |

OTHER PUBLICATIONS

Printout from Sigma-Aldrich, "P8136 Poly(vinyl alcohol)" Product Specification sheet; obtained from Sigma-Aldrich online catalog Jun. 4, 2018. (Year: 2018).*
Ng et al. Nature Protocols 3(5):768-776, 2008 (Year: 2008).*
Extended European Search Report dated Jul. 17, 2017 in European Patent Application No. 14887887.9.
Li-Jun Wang, et al., "Defined media optimization for in vitro culture of bovine somatic cell nuclear transfer (SCNT) embryos", Theriogenology, vol. 78 No. 9, XP055388371, Dec. 1, 2012, pp. 2110-2119.
Gisele Zoccal Mingoti, et al., "The effects of macromolecular and serum supplements and oxygen tension during bovine in vitro procedures on kinetics of oocyte maturation and embryo development", In Vitro cellular & Developmental Biology—Animal, vol. 47 No. 5-6, XP019912098, Mar. 18, 2011, pp. 361-367.
Kazutoshi Takahashi, et al., "Induction of Pluripotent Stem Cells from Adult Human Fibroblasts by Defined Factors" Cell, vol. 131, No. 5, Nov. 30, 2007, pp. 861-872.
Junying Yu, et al., "Induced Pluripotent Stem Cell Lines Derived from Human Somatic Cells" Science, vol. 318, No. 5858, Dec. 21, 2007, pp. 1917-1920.
Elizabeth S. Ng, et al., "A protocol describing the use of a recombinant protein-based, animal product-free medium ( APEL) for human embryonic stem cell differentiation as spin embryoid bodies" Nature Protocols, vol. 3, No. 5, 2008, pp. 768-776.
Sigma-Aldrich, "P8136 Poly(vinyl alcohol)", Retrieved from URL: http://www.sigmaaldrich.com/catalog/product/sial/p8136?lang=jaRion= JP, Retrieved on Nov. 10, 2014, 2 Pages.
Office Action dated Apr. 11, 2017 in Japanese Patent Application No. 2016-511307 (with English language translation).
Kong Lijuan, China Master's Theses Full-text Database, fundamental science; No. 5, A006-92, 2008 (including English abstract).
Wang Gai-Zhen et al., Chemical Journal of Chinese Universities, vol. 30, No. 1, 68-71, 2009 (including English abstract).

* cited by examiner

Primary Examiner — Marcia S Noble
(74) Attorney, Agent, or Firm — Oblon, McClelland, Maier & Neustadt, L.L.P.

(57) ABSTRACT

Culture media which contain a water-soluble polymer, such as polyvinyl alcohol and the like, and albumin, and the like, are useful for the proliferation of stem cells, and show good culture results, particularly with iPS cells, and maintain the stability of the medium properties, as well as using a reduced amount of albumin.

15 Claims, 1 Drawing Sheet

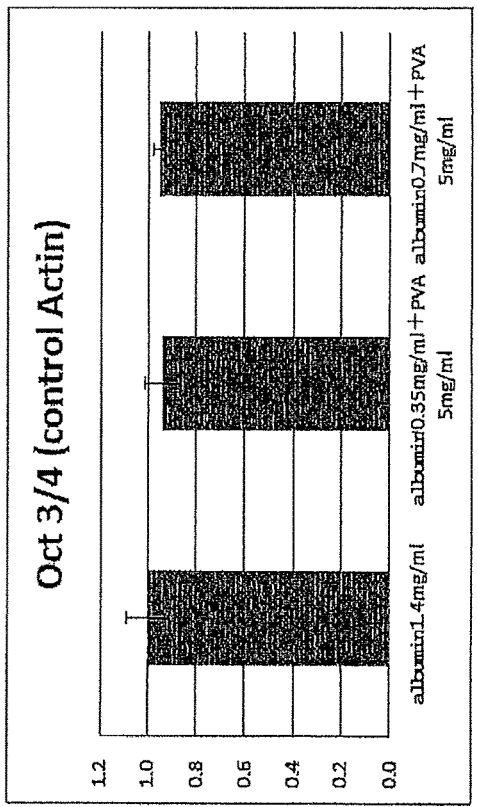
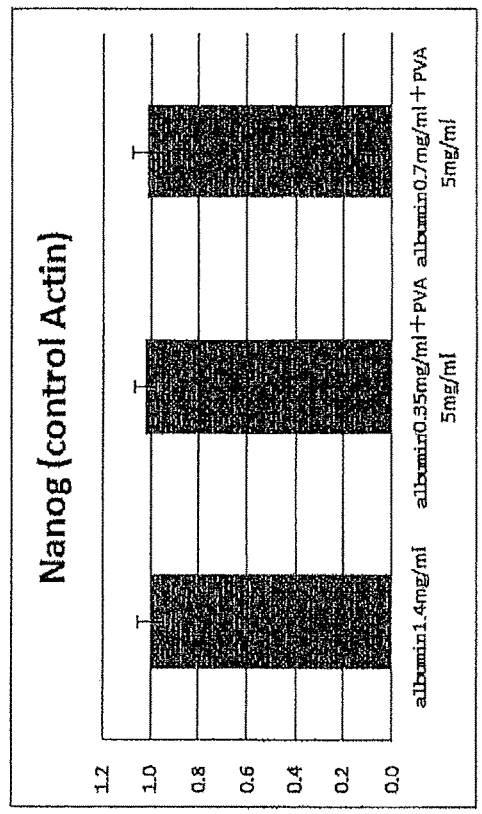
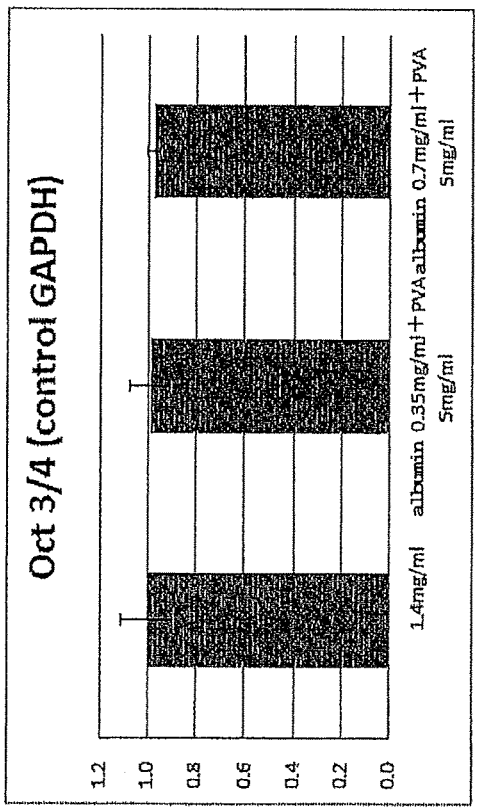
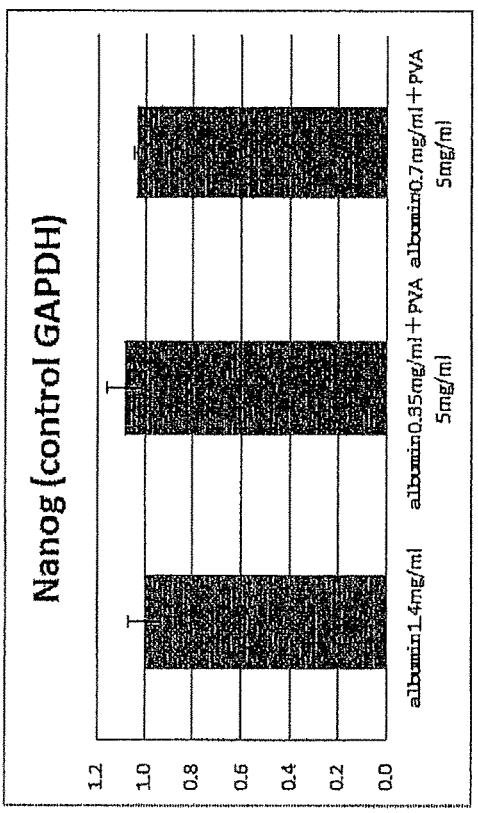

MEDIUM FOR STEM CELL USE

CROSS REFERENCES TO RELATED APPLICATIONS

This application is a continuation of International Patent Application No. PCT/JP2014/071256, filed on Aug. 12, 2014, and claims priority to Japanese Patent Application No. 2014-070763, filed on Mar. 31, 2014, both of which are incorporated herein by reference in their entireties.

BACKGROUND OF THE INVENTION

Field of the Invention

The present invention relates to media for stem cells, a method of producing such a medium, and the like.

Discussion of the Background

Conventionally, the culture of stem cells (embryonic stem cell, induced pluripotent stem cell (iPS cell) and the like) has been conducted using a medium containing a serum. For example, fetal bovine serum (FBS) and the like are widely used for cell culture as an important additive for cell proliferation. However, when stem cells after culture are used for medical purposes, a xeno-derived component may become a source of infection with blood-borne pathogen or a xenoantigen. In addition, culture results may be inconsistent due to differences between serum lots. Therefore, it is mainstream in recent years to use a medium having a clear chemical composition (chemically-defined medium) for culturing stem cells, and the development of a serum-free medium is ongoing.

One of the highly important components for serum-free medium is albumin. Addition of albumin is expected to provide an effect of stably maintaining the medium property. Several kinds of albumin are commercially available for culturing cells. However, albumin is comparatively expensive, not all albumins provide an equivalent effect for cell culture, particularly culture of stem cells, and the quality of albumin affects the culture results; in some cases, addition of albumin unfavorably acts on the cell growth. Furthermore, degradation of albumin in the medium has also posed a problem.

As a comparatively economical albumin, an albumin extracted from a serum of animals such as human, bovine and the like can be mentioned. However, when the donor is infected with a virus and the like, the risk of dissemination thereof exists. Therefore, use of such albumin derived from animal serum for clinical application is markedly limited and, even when use is permitted, the amount thereof to be used is required to be extremely low.

Albumin produced by a gene recombination (recombinant) method considered to be preferable for use for clinical application due to its low infection risk is considerably expensive. When a sufficient amount of cells is to be secured by subjecting such albumin to cell culture, the cost becomes extremely high. To use such recombinant albumin in cell culture, therefore, the amount thereof to be used is required to be extremely small.

Accordingly, the development of a medium using a reduced amount of albumin or free of albumin has been tried. For example, JP-A-2004-135672, which is incorporated herein by reference in its entirety, reports on the use of polyethylene glycol as an albumin substitute in a medium. JP-A-2007-228815, which is incorporated herein by reference in its entirety, reports on a polyvinyl alcohol-containing medium characteristically free of albumin. US 2010/0317104A1, which is incorporated herein by reference in its entirety, reports on the use of polyvinyl alcohol in a medium for embryonic stem cells (HESCs). WO 2011/100286A2, which is incorporated herein by reference in its entirety, reports that polyvinyl alcohol and the like are used in a medium for differentiation of mesoderm stem cells from pluripotent cells.

However, there remains a need for improved culture media for culturing stem cells.

SUMMARY OF THE INVENTION

Accordingly, it is one object of the present invention to provide novel growth media for stem cell cells.

It is another object of the present invention to provide novel growth media for stem cells showing good culture results.

It is another object of the present invention to provide novel growth media for stem cells, particularly an iPS cell, which maintains stability of medium property as well as carries a reduced amount of albumin.

It is another object of the present invention to provide medium additives for producing such a growth medium, and an agent for preventing degradation of such a medium.

These and other objects, which will become apparent during the following detailed description, have been achieved by the inventors' discovery that the albumin content can be reduced and superior culture results can be obtained by using a water-soluble polymer having specific properties, particularly polyvinyl alcohol, in combination in an albumin-containing medium.

Accordingly, the present invention provides:

(1) A medium for culturing an iPS cell, comprising a water-soluble polymer and an albumin.

(2) The medium of the above-mentioned (1), wherein the water-soluble polymer is polyvinyl alcohol.

(3) The medium of the above-mentioned (2), wherein the polyvinyl alcohol has a critical micelle concentration of 0.1 to 5 mg/ml.

(4) The medium of the above-mentioned (2) or (3), wherein the polyvinyl alcohol has a hydrolysis ratio of 60 to 95%.

(5) The medium of any of the above-mentioned (1) to (4), wherein the albumin carries a reduced amount of fatty acid.

(6) A medium additive comprising a water-soluble polymer as an active ingredient.

(7) The agent of the above-mentioned (6), wherein the water-soluble polymer is polyvinyl alcohol.

(8) The agent of the above-mentioned (7), wherein the polyvinyl alcohol has a critical micelle concentration of 0.1 to 5 mg/ml.

(9) The agent of the above-mentioned (7) or (8), wherein the polyvinyl alcohol has a hydrolysis ratio of 60 to 95%.

(10) The agent of any of the above-mentioned (6) to (9), wherein the medium is an albumin-containing medium.

(11) The agent of the above-mentioned (10), wherein the albumin carries a reduced amount of fatty acid.

(12) The agent of any of the above-mentioned (6) to (11), wherein the medium is a medium for proliferation of stem cells.

(13) The agent of the above-mentioned (12), wherein the stem cell is an iPS cell.

(14) The agent of any of the above-mentioned (6) to (13), which is an agent for prevention of degradation of an albumin-containing medium.

(15) A method of preventing degradation of an albumin-containing medium, comprising adding a water-soluble polymer.

(16) The method of the above-mentioned (15), wherein the water-soluble polymer is polyvinyl alcohol.

(17) A method of culturing an iPS cell, comprising culturing in the culture medium of any of the above-mentioned (1) to (5).

Using the medium of the present invention, the amount of albumin in a medium can be reduced. Therefore, the stability of medium properties can be maintained by adding a lower dose of albumin. A lower dose of albumin enables more safe and more stable growth of stem cells. Consequently, the frequency of medium exchange during culture can be reduced, and the cost of stem cell culture can be decreased.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 is confirms that an iPS cell grown by the culture method of the present invention has undifferentiated properties.

DETAILED DESCRIPTION OF THE PREFERRED EMBODIMENTS

In the present invention, the term "stem cell" means an immature cell having self-renewal capacity and differentiation/proliferation capacity. The stem cell includes subpopulations such as pluripotent stem cell, multipotent stem cell, unipotent stem cell and the like, according to the differentiation potency. The pluripotent stem cell means a cell capable of differentiating into any tissue or cell constituting living organisms. The multipotent stem cell means a cell capable of differentiating into plural, though not all, kinds of tissues and cells. The unipotent stem cell means a cell capable of differentiating into specific tissues and cells.

Examples of the pluripotent stem cell include embryonic stem cells (ES cell), embryonic germ cell (EG cell), induced pluripotent stem cell (iPS cell), pluripotent stem cell induced and selected by stress or cell stimulation and the like. A stem cell established by cultivating an early embryo generated by nuclear transplantation of the nucleus of a somatic cell is also preferable as the pluripotent stem cell (see Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA, 96, 14984 (1999); Nature Genetics, 24, 109 (2000) all of which are incorporated herein by reference in their entireties).

Examples of the multipotent stem cell include somatic stem cells such as mesenchymal stem cell, hematopoietic stem cell, neural stem cell, myeloid stem cell and germ line stem cell, and the like. The multipotent stem cell is preferably a mesenchymal stem cell, more preferably a bone marrow mesenchymal stem cell. The mesenchymal stem cell broadly means a population of stem cells or progenitor cells thereof, which can differentiate into all or some of the mesenchymal cells, such as osteoblast, chondroblast, lipoblast and the like.

As the basal medium to be used in the present invention, one known per se can be used, and is not particularly limited as long as it does not inhibit proliferation of the stem cells. Examples thereof include DMEM, EMEM, IMDM (Iscove's Modified Dulbecco's Medium), GMEM (Glasgow's MEM), RPMI-1640, α-MEM, Ham's Medium F-12, Ham's Medium F-10, Ham's Medium F12K, Medium 199, ATCC-CRCM30, DM-160, DM-201, BME, Fischer, McCoy's 5A, Leibovitz's L-15, RITC80-7, MCDB105, MCDB107, MCDB131, MCDB153, MCDB201, NCTC109, NCTC135, Waymouth's MB752/1, CMRL-1066, Williams' medium E, Brinster's BMOC-3 Medium, E8 medium (Nature Methods, 2011, 8, 424-429), ReproFF2 medium (ReproCELL Inc), a mixed medium thereof and the like. In addition, a medium altered for culture of stem cells, a mixture of the above-mentioned basal medium and other medium, and the like may also be used.

In the present invention, the "albumin-containing medium" is the above-mentioned basal medium added with an albumin ("albumin" is described later).

In the present invention, "degradation of albumin-containing medium" refers to a state where an ability to support cell proliferation and an ability to maintain an undifferentiated state of a cell are degraded compared to an albumin-containing medium immediately after preparation. Specifically, it means a phenomenon that, when an albumin-containing medium is prepared and used for culture after the lapse of a given period, the number of grown cultured cells, the amount of undifferentiated marker and the like become lower than those when cultured in a medium immediately after preparation. The cause of such phenomenon is, for example, the amount of albumin in the medium which becomes insufficient for an effective action in cell culture due to the decomposition and denaturation of albumin in the medium, adsorption to a medium container and the like during lapse of a given period after preparation of the medium.

The medium to be used in the present invention can contain an additive substance known per se. The additive substance is not particularly limited as long as it does not inhibit proliferation of stem cells. Examples thereof include growth factor (e.g., insulin etc.), iron source (e.g., transferrin etc.), polyamines (e.g., putrescine etc.), mineral (e.g., sodium selenate etc.), saccharides (e.g., glucose etc.), organic acid (e.g., pyruvic acid, lactic acid etc.), amino acid (e.g., L-glutamine), reducing agent (e.g., 2-mercaptoethanol), vitamins (e.g., ascorbic acid, d-biotin etc.), steroid (e.g., β-estradiol, progesterone etc.), antibiotic (e.g., streptomycin, penicillin, gentamicin etc.), buffering agent (e.g., HEPES etc.) and the like. In addition, additives that have been conventionally used for culturing stem cells can be contained as appropriate. The additive is preferably contained within a concentration range known per se.

The medium to be used in the present invention may contain a serum. Serum is not particularly limited as long as it is derived from an animal and does not inhibit the growth of stem cells. Preferred is a mammal-derived serum (e.g., fetal bovine serum, human serum etc.). The concentration of the serum may be any as long as it is within a concentration range known per se. However, a lower content of serum is more preferable, and the absence of serum is most preferable, since it is known that serum components also contain a differentiation factor of human ES cell, and the like, and the culture results may be inconsistent due to a difference between serum lots. Furthermore, when a stem cell after culture is used for medical purposes, a xeno-derived component may become an infection source of blood-mediated pathogen or a xenoantigen. Therefore, the absence of serum is preferable. When serum is not contained, a replacement additive of serum (e.g., Knockout Serum Replacement (KSR) (Invitrogen), Chemically-defined Lipid concentrated (Gibco), Glutamax (Gibco) etc.) may also be used.

The present invention provides a medium for proliferation of stem cells, particularly iPS cells, which characteristically contains a water-soluble polymer and an albumin (hereinafter to be also referred to as the medium of the present invention). A medium for proliferation is a medium that enables replication (i.e., proliferation) of a stem cell while maintaining the replication competence, pluripotency and unipotency of the cell.

1. Medium of the Present Invention

While the medium of the present invention can be preferably used for proliferation of any stem cells, it is preferably used for proliferation of ES cell or iPS cell, more preferably iPS cell.

Also, the medium of the present invention can be preferably used for proliferation of stem cells derived from any animals. The stem cells cultured by using the medium of the present invention are, for example, stem cells derived from rodents such as mouse, rat, hamster, guinea pig and the like, Lagomorpha such as rabbit and the like, Ungulata such as swine, bovine, goat, horse, sheep and the like, Carnivora such as dog, cat and the like, primates such as human, monkey, Macaca mulatta, marmoset, orangutan, chimpanzee and the like. Preferred are stem cells derived from human.

The albumin to be used in the present invention is not particularly limited as long as it is used for cell culture, and one carrying a reduced amount of fatty acid is preferably used. It is directly added to a medium when the amount of fatty acid to be carried is already reduced, or added after a fatty acid removal treatment when the amount of fatty acid to be carried has not been reduced.

Examples of the fatty acids include saturated fatty acids having 8 to 20 carbon atoms (e.g., palmitic acid, stearic acid) and unsaturated fatty acids having 16 to 20 carbon atoms (e.g., oleic acid, linoleic acid, linolenic acid, arachidonic acid).

Specific examples of albumin include naturally-derived albumin such as ovalbumin, swine-derived albumin, bovine-derived albumin and human-derived albumin, gene recombinant albumin such as bovine type, swine type and human type, and the like. Particularly preferable examples thereof include serum-derived albumin and human type gene recombinant albumin (recombinant human albumin (rHSA)). A commercially available one can be utilized. Examples of commercially available one include products derived from recombinant rice such as A9731 (model number) of Sigma-Aldrich, OsrHSA-10 (model number) of ScienCell Research Laboratories, HY01E-10 g (model number) of Wuhan Healthgen Biotechnology Co., Ltd., HSA-1r (model number) of E Enzyme Inc.), IBK-A1-10 (model number) of BioVerde and the like, products derived from recombinant yeast such as A7223 (model number), A6608 (model number), A7736 (model number) of Sigma-Aldrich, Albucult (registered trade mark) (product name), Recombumin alpha (registered trade mark) (product name), AlbIX (registered trade mark) (product name) and the like of Novozymes, as rHSA. Examples of albumin derived from human plasma include products such as A1887 (model number), A1653 (model number), A9511 (model number), A3782 (model number), A8763 (model number), A4327 (model number) of Sigma-Aldrich, Bio-Pure HSA 10% Solution (product name) of Biological Industries Ltd. and the like.

Albumin is a protein having a high ability to bind to various substances, and binds to minerals such as calcium, zinc and the like, fatty acid, enzyme, hormone and the like. For example, serum-derived albumin binds to various substances contained in serum. In the case of fatty acid, 1 molecule of albumin generally has an ability to bind to 2 molecules of fatty acid.

The fatty acid removal treatment of albumin is not particularly limited as long as it can reduce the amount of fatty acid binding to albumin, and a treatment with activated carbon, an ion exchange treatment, a heat treatment and the like can be mentioned. From the aspects of economic efficiency, convenience and the like, a treatment with activated carbon is preferable. By an activated carbon treatment, the amount of fatty acid binding to albumin can be reduced to preferably not more than 9 mg, more preferably not more than 7 mg, further preferably not more than 2.2 mg, per 1 g of albumin.

The amount of fatty acid binding to albumin can be measured by a method generally practiced in the pertinent field, or a method analogous thereto. Examples thereof include methyl esterification of free fatty acid followed by detection by GC-MS, quantification by infrared spectroscopy and extraction method of Duncombe, ACS-ACOD method using acyl-CoA synthase (ACS) and acyl-CoA oxydase (ACOD) and the like. A commercially available measurement kit can be utilized for any of these.

In the present invention, the content of albumin in a medium is not particularly limited as long as it is an amount generally added to a medium for cell culture. In the present invention, the content thereof can be reduced by using in combination with a water-soluble polymer. Specifically, it is added to a basal medium for stem cell culture to a final concentration of 0.01 to 10 mg/ml, preferably 0.1 to 5 mg/ml, more preferably 0.2 to 3.5 mg/ml, further preferably 0.3 to 3 mg/ml. When the content is too small, the effect of maintaining stability of the medium properties cannot be expected and, when it is too high, the production cost of the medium becomes too high to reduce practicability.

Since albumin is considered to form a three-dimensional structure in the medium and exhibits various functions including the role of a carrier of a liposoluble substance, it is assumed that the functions of albumin can be substituted or aided by mimicking such steric structure. A compound can have a steric structure by assembling compounds having surface activation functions by micelle formation. Therefore, a possibility of substituting or aiding albumin by micelle formation is considered. In this respect, in the present invention, a water-soluble polymer can be a substitute or aid of albumin by a micelle forming ability thereof.

The water-soluble polymer to be used in the present invention is one capable of being used for cell culture, that is, one free of cytotoxicity, and capable of reducing the amount of albumin by combined use with albumin. In one embodiment of a water-soluble polymer to be used in the present invention, the critical micelle concentration (CMC) is 0.1 to 10 mg/ml, preferably 0.1 to 5 mg/ml, more preferably 0.5 to 1 mg/ml. One embodiment of the water-soluble polymer to be used in the present invention is polyvinyl alcohol, having CMC of 0.1 to 5 mg/ml, preferably 0.5 to 5 mg/ml, more preferably 0.5 to 1 mg/ml. As used herein, micelle is an assembly of water-soluble polymer molecules that can be formed by gathering of a given number of molecules due to the orientation of the hydrophilic group moiety toward the aqueous phase side and the hydrophobic group moiety toward the inside in an aqueous solution. In the present invention, "micelle" encompasses not only a micelle in such narrow sense, but also colloidal coagulation referred to as a pseudo-micelle (see, e.g., Revue Roumaine de Chimie, vol. 54, pages 577-581, 2009, which is incorporated herein by reference in its entirety). When the CMC is too low, its extremely high micelle formability is feared to coagulate surfactants and the like contained in the medium to influence the cell culture. When it is too high, micelle formation requires addition of a large amount of the water-soluble polymer, in which case the viscosity and osmotic pressure of the medium are feared to increase and influence the cultured cells. A lower CMC shows higher micelle formability.

The measurement of CMC can be performed by a method generally performed in the pertinent field or a method analogous thereto. For example, it can be measured by an electric conductive method, a viscosity method, a dye method, a surface tension method, a photoscattering method and the like. In recent years, a method for calculation by measuring the fluorescence intensity by using a fluorescent substance pyrene is also used.

Specific examples of the water-soluble polymer to be used in the present invention include polyvinyl alcohol (PVA), polyethylene glycol (PEG) and the like, with preference given to PVA.

PVA used as a water-soluble polymer in the present invention preferably shows a hydrolysis ratio of 60 to 95%, preferably 70 to 90%, more preferably 75 to 90%. The hydrolysis ratio here is a ratio of conversion of an acetyl group of polyvinyl acetic acid to be the starting material of PVA to a hydroxyl group by hydrolysis. A higher % shows more advanced hydrolysis. When the hydrolysis ratio is too low, water-solubility is not sufficient and, when it is too high, hydroxyl groups of polymers form a hydrogen bond to lower the solubility and dispersibility in water. To enable more uniform contact with cells, PVA in the form of a solution is preferably used. While a solvent to be used to produce a solution is not particularly limited as long as it can be added to a cell culture medium and does not show an adverse effect on the cell proliferation, water, physiological buffer and the like can be mentioned.

The water-soluble polymer typically has a weight or number average molecular weight of 1,000 to 500,000, preferably 1,500 to 100,000, more preferably 10,000 to 50,000.

The water-soluble polymer typically has a viscosity of 0.5 to 50, preferably 1.5 to 30, more preferably 2 to 10 ($mm^2/s$).

In the present invention, the content of a water-soluble polymer in a medium is not particularly limited as long as it is an amount generally added to a medium for cell culture. Specifically, when the water-soluble polymer is PVA, it is added to a basal medium for stem cell culture to a final concentration of 0.1 to 20 mg/ml, preferably 1 to 20 mg/ml, more preferably 1 to 10 mg/ml, further preferably 3 to 7 mg/ml. The ratio of the contents of albumin and water-soluble polymer in the medium can be appropriately adjusted by the kind of water-soluble polymer to be used. For example, when the water-soluble polymer is PVA, it can be 1:1.1 to 100, preferably 1:1.1 to 50, more preferably 1:1.1 to 25, further preferably 1:3 to 15. When the content is too small, the effect as an albumin substitute cannot be expected and, when it is too high, cytotoxicity is feared.

The present invention provides a medium additive containing a water-soluble polymer as an active ingredient (hereinafter to be also referred to as the medium additive of the present invention).

2. Medium Additive of the Present Invention

The water-soluble polymer to be used for the medium additive of the present invention is the same as those used for the above-mentioned "1. Medium of the present invention". The medium additive of the present invention containing a water-soluble polymer is added in an amount necessary for a basal medium and the like. Since it can substitute for albumin in maintaining the medium properties, it is particularly suitable for addition to a medium containing albumin. Here, albumin to be contained in the medium is the same as those used for the above-mentioned "1. Medium of the present invention".

The medium additive of the present invention can contain, besides a water-soluble polymer as an active ingredient, various factors preferably added to a medium. For example, the additives known per se which are recited as examples in the above-mentioned "1. Medium of the present invention" can be contained.

The medium additive of the present invention can be an albumin substitute in maintaining the medium properties, namely, has an effect of preventing degradation of a medium. Therefore, the medium additive of the present invention can also be preferably used as an agent for preventing degradation of an albumin-containing medium.

The amount of the medium additive of the present invention to be added to a basal medium is appropriately selected according to a desired effect and the kind of the water-soluble polymer to be added. For example, when the medium additive wherein PVA is used as a water-soluble polymer and added to an albumin-containing medium, for example, an albumin-containing medium for growth culture of stem cells (particularly iPS cells), it is added generally at 0.1 to 20 mg/ml, preferably 1 to 20 mg/ml, more preferably 1 to 10 mg/ml, further preferably 3 to 7 mg/ml, in the amount of a water-soluble polymer as the active ingredient. The content ratio of albumin and water-soluble polymer in the medium after final adjustment can be 1:1.1 to 100, preferably 1:1.1 to 50, more preferably 1:1.1 to 25, further preferably 1:3 to 15.

The present invention provides a method of culturing stem cells (hereinafter to be also referred to as the culture method of the present invention).

3. Culture Method of the Present Invention

The culture method of the present invention includes a step of cultivating stem cells (preferably, iPS cells) in the medium of the present invention (see the above-mentioned "1. Medium of the present invention").

While a culture container to be used for the culture of stem cell is not particularly limited as long as stem cells can be cultured, a flask, tissue culture flask, dish, petri dish, tissue culture dish, multidish, microplate, microwell plate, multiplate, multiwell plate, microslide, chamber slide, Schale, tube, tray, culture bag and roller bottle can be mentioned.

The culture container may be cell adhesive or cell non-adhesive, and is appropriately selected according to the object. A cell adhesive culture container may be coated with any cell supporting substrate such as extracellular matrix (ECM) and the like, in an attempt to improve the adhesiveness of the culture container surface to a cell. The cell supporting substrate may be any substance aiming at adhesion of stem cell or feeder cell (when used).

Other culture conditions can be appropriately determined. For example, while the culture temperature is not particularly limited, it can be about 30 to 40° C., preferably about 37° C. The $CO_2$ concentration can be about 1 to 10%, preferably about 2 to 5%. The oxygen partial pressure can be 1 to 10%.

In the culture method of the present invention, culture of stem cells in the medium of the present invention, or the timing of addition of the medium additive of the present invention to stem cell culture is not particularly limited as long as a desired stem cell proliferation promoting effect can be obtained. For example, stem cells may be seeded in the medium of the present invention, or stem cells may be seeded in an albumin-containing medium, cultured for one to several days, preferably one day, and the medium additive of the present invention may be added to the medium. Alternatively, the medium may be exchanged with the medium of the present invention.

iPS cells grown by the culture method of the present invention maintain undifferentiated properties. As a method for confirming whether iPS cell has undifferentiated properties, confirmation method using an undifferentiated marker as an index can be mentioned. Examples of the undifferentiated marker include alkaline phosphatase, Oct3/4, Sox2, Nanog, ERas, Esgl and the like. As a method for detecting these undifferentiated markers, a method of detecting mRNA, an immunological detection method and the like can be mentioned.

Other features of the invention will become apparent in the course of the following descriptions of exemplary embodiments which are given for illustration of the invention and are not intended to be limiting thereof.

EXAMPLES

Materials and Methods
1. Polyvinyl Alcohol (PVA)
The following PVAs were used. Manufactured by The Nippon Synthetic Chemical Industry Co., Ltd.:
    Gohsenol EG-05PW (hydrolysis ratio 88%)
    Gohsenol NL-05 (hydrolysis ratio 99%)
    Gohsenol KL-05 (hydrolysis ratio 79%)
    Gohsenol EG-03P (hydrolysis ratio 88%)

Manufactured by ACROS Organics:
  302780250 (hydrolysis ratio 78%)
Manufactured by Kanto Chemical Co., Inc.:
  32283-02 (hydrolysis ratio 86.5-89%).
2. Albumin
  Recombinant human albumin manufactured by Novozymes was used.
  product name: Recombumin and Albucult
  Human serum albumin manufactured by Baxter was used after treatment with activated carbon (manufactured by Wako Pure Chemical Industries, Ltd.). The amount of fatty acid (quantified using LabAssay NEFA: manufactured by Wako Pure Chemical Industries, Ltd.) binding to albumin decreased to 1 to 2 mg per 1 g albumin by the activated carbon treatment.
3. Measurement of Critical Micelle Concentration (CMC)
  The critical micelle concentration (CMC) of PVA was calculated by a fluorescence intensity measurement method using a fluorescent substance pyrene, based on the method described in Journal of Controlled Release, vol. 143, page 201-206, 2010, which is incorporated herein by reference in its entirety. PVA aqueous solutions having different concentrations (0.01 to 50 mg/ml) were mixed with 6 mM pyrene/acetone solution, and the mixture was shaken at room temperature for 1 hr. The fluorescence intensity of the mixture at emmision wavelength 390 nm to that at excitation wavelengths 333 nm and 339 nm was measured (I-333 and I-339). The fluorescence intensity ratio relative to PVA concentration (I-339/I-333) was plotted, and PVA concentration at which the fluorescence intensity ratio sharply increased was taken as CMC. The results are shown in Table 1.

TABLE 1

Measurement results of critical micelle oncentration CMC of various PVAs

| PVA | CMC (mg/ml) |
|---|---|
| Gohsenol KL-05 | 0.5-1 |
| Gohsenol EG-05PW | 1 |
| Gohsenol NL-05 | 20 |
| Gohsenol EG-03P | 1 |
| 302780250 | 1 |
| 32283-02 | 0.5-1 |

Results

Example 1

Evaluation in iPS Cell Proliferation System—1

Using various water-soluble polymers, a proliferative effect on induced pluripotent stem cells (iPS cells) was evaluated. As the iPS cell, 201B7 strain purchased from iPS Academia Japan, Inc. was used. Cell culture was performed under conditions of 5% $CO_2$/37° C. and using a culture vessel (Nippon Becton Dickinson Company, Ltd., Falcon culture petri dish or Falcon culture plate) coated with a basal membrane matrix (Matrigel manufactured by Nippon Becton Dickinson Company, Ltd.,). Various PVAs and various albumins were added at given concentrations to Essential 8 medium (manufactured by Invitrogen), which is a feederless medium for iPS cell, to give a test medium. These were used for culture immediately or after preservation at 4° C. for 2 to 4 weeks, and the effects thereof were studied. Y-27632 was added (final concentration 10 μM, NACALAI TESQUE, INC.: 08945-84) to a medium to be used for seeding. From the next day, the cells were cultured in a test medium without Y-27632. The medium was exchanged every 2 to 3 days and, after culture for 1 week, the cell number was measured. The cell number was measured by the method described in "Kaitei Saibou baiyou Nyumon Note, pages 77-83, 2010, YODOSHA CO., LTD." which is incorporated herein by reference in its entirety. As a control, similar culture was performed in a medium added with albumin alone and not added with PVA.

The evaluation criteria were as follows.

⊙: number of cells is not less than 150% of that of control

○: number of cells is not less than 120% and less than 150% of that of control

□: number of cells is not less than 100% and less than 120% of that of control

–: number of cells is not less than 50% and less than 100% of that of control

X: number of cells is less than 50% of that of control

The results are shown in Tables 2 to 4.

TABLE 2

Cell evaluation results of Essential 8 medium added with PVA and Recombumin

| PVA | Recombumin concentration (mg/ml) | used for culture immediately after preparation of test medium | | | used for culture after preparation and preservation at 4° C. for 2 weeks of test medium | | |
|---|---|---|---|---|---|---|---|
| | | PVA 1 mg/ml | PVA 5 mg/ml | PVA 20 mg/ml | PVA 1 mg/ml | PVA 5 mg/ml | PVA 20 mg/ml |
| Gohsenol KL-05 | 0.35 | — | ○ | ⊙ | X | □ | ⊙ |
| | 0.7 | — | □ | ⊙ | — | ○ | ⊙ |
| | 1.4 | — | ⊙ | ⊙ | □ | ⊙ | ⊙ |
| Gohsenol EG-05PW | 0.35 | — | □ | ○ | — | □ | ⊙ |
| | 0.7 | — | □ | ⊙ | — | ○ | ⊙ |
| | 1.4 | □ | ⊙ | ⊙ | — | ○ | ⊙ |
| Gohsenol NL-05 | 0.35 | — | □ | ⊙ | — | — | ⊙ |
| | 0.7 | X | — | ⊙ | — | □ | ⊙ |
| | 1.4 | — | □ | ⊙ | — | □ | ⊙ |

TABLE 3

Cell evaluation results of Essential 8 medium added with PVA and Albucult

| PVA | Albucult concentration (mg/ml) | used for culture immediately after preparation of test medium PVA 1 mg/ml | used for culture immediately after preparation of test medium PVA 5 mg/ml | used for culture after preparation and preservation at 4° C. for 2 weeks of test medium PVA 1 mg/ml | used for culture after preparation and preservation at 4° C. for 2 weeks of test medium PVA 5 mg/ml |
|---|---|---|---|---|---|
| Gohsenol KL-05 | 0.35 | — | □ | □ | ⊙ |
| | 0.7 | — | ○ | ○ | ○ |
| | 1.4 | □ | ⊙ | ○ | ⊙ |
| Gohsenol EG-05PW | 0.35 | □ | ○ | □ | ⊙ |
| | 0.7 | □ | ○ | ⊙ | ⊙ |
| | 1.4 | □ | ⊙ | — | ⊙ |
| Gohsenol NL-05 | 0.35 | — | — | □ | □ |
| | 0.7 | — | ○ | — | ○ |
| | 1.4 | — | ○ | — | — |

TABLE 4

Cell evaluation results of Essential 8 medium added with PVA and human serum albumin

| PVA | human serum albumin concentration (mg/ml) | used for culture immediately after preparation of test medium PVA 1 mg/ml | used for culture immediately after preparation of test medium PVA 5 mg/ml | used for culture after preparation and preservation at 4° C. for 2 weeks of test medium PVA 1 mg/ml | used for culture after preparation and preservation at 4° C. for 2 weeks of test medium PVA 5 mg/ml |
|---|---|---|---|---|---|
| Gohsenol EG-05PW | 0.35 | ○ | ⊙ | — | — |
| | 0.7 | ○ | ⊙ | ⊙ | ⊙ |
| | 1.4 | ⊙ | ⊙ | ⊙ | ⊙ |

As shown in Table 1, with PVA having a hydrolysis ratio is 79% or 88%, the CMC is not more than 1 mg/ml, which is clearly a low concentration as compared to CMC (20 mg/ml) of PVA with hydrolysis ratio of 99%, and therefore, micelle formability is high.

As shown in Tables 2 and 3, PVA with hydrolysis ratio of 79% or 88% showed good iPS cell growth promoting activity at both addition concentrations of 1 mg/ml and 5 mg/ml, as compared to PVA with hydrolysis ratio of 99%. Particularly, at an addition concentration of 5 mg/ml, the frequency of the cell number being not less than 120% relative to that of the control is 9 samples out of 12 samples when the PVA has a hydrolysis ratio of 79% or 88%, and 3 samples out of 12 samples when the PVA has a hydrolysis ratio of 99%, therefore, the difference in the effect is made obvious.

As shown in Table 4, PVA with a hydrolysis ratio of 88% showed good iPS cell growth promoting activity when added with human serum albumin.

Example 2

Evaluation in iPS Cell Proliferation System—2

The iPS cell growth effect in an albumin-containing medium was evaluated using PVA as a water-soluble polymer. Gohsenol EG-05PW was used as PVA, and human serum albumin was used as albumin. Obtainment and culture of iPS cell were performed in the same manner as in Example 1. PVA and albumin were added at given concentrations to Essential 8 medium (manufactured by Invitrogen), which is a feederless medium for iPS cell, to give a test medium. This was used for culture immediately or after preservation at 4° C., for 3 weeks, and the effect thereof was studied. Y-27632 was added (final concentration 10 μM, NACALAI TESQUE, INC.: 08945-84) to a medium to be used for seeding. From the next day, the cells were cultured in a test medium without Y-27632. The medium was exchanged every 2 to 3 days and, after culture for 1 week, the cell number was measured. The cell number was measured in the same manner as in Example 1. As a control, similar culture was performed in a medium added with albumin (1.4 mg/ml) alone and not added with PVA.

The evaluation criteria were as described below.
As compared to the control:
⊙: significantly high cell proliferation capacity
○: equivalent cell proliferation capacity
Δ: significantly low cell proliferation capacity
The results are shown in Table 5.

TABLE 5

Cell evaluation results of Essential 8 medium added with PVA and human serum albumin

| | albumin (Alb) used for culture immediately after preparation of test medium | albumin (Alb) used for culture after preparation and preservation at 4° C. for 3 weeks of test medium |
|---|---|---|
| Alb 0.35 mg/ml + PVA 5 mg/ml | ○ | ○ |
| Alb 0.7 mg/ml + PVA 5 mg/ml | ○ | ○ |
| Alb 1.4 mg/ml + PVA 5 mg/ml | ⊙ | ⊙ |

Example 3

Measurement of Undifferentiated Marker

Measurement Method
Analysis of mRNA Expression by Real-Time PCR Method
Cells cultured in various test media were recovered, and total RNAs in the cells extracted using RNeasy Plus Mini Lit (manufactured by Qiagen). cDNA was synthesized by reverse transcription reaction using each extracted total RNA as a template and PrimerScript RT reagent Kit (manufactured by Takara Bio Inc.). PCR was performed by 7500 Fast Real Time PCR system (manufactured by Applied Biosystems) using this cDNA template, various forward primers and reverse primers (synthesis of both was committed to Hokkaido System Science Co., Ltd.), and Power SYBR Green PCR Master Mix (manufactured by Applied Biosystems). The mRNA expression level was normalized by endogenous control β-actin (ActB) or GAPDH (glyceraldehyde 3-phosphate dehydrogenase).

Results
The results are shown in FIG. 1. As shown in FIG. 1, the expression levels of Oct3/4 and Nanog, which are representative undifferentiated markers of iPS cell, did not change even when PVA was added and albumin amount was reduced.

From the above results, it was confirmed that PVA does not influence the undifferentiated potency of iPS cells.

INDUSTRIAL APPLICABILITY

Using the medium of the present invention, stem cells can be efficiently proliferated, the frequency of exchange of culture medium can be reduced, and the culture cost of stem cells can be decreased.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A medium for culturing an iPS cell, comprising:
polyvinyl alcohol; and
an albumin,
wherein the albumin and the polyvinyl alcohol are included in the medium in a weight ratio of 1:1.1 to 100, and
an amount of fatty acid binding to the albumin is not more than 2.2 mg per 1 g of the albumin.

2. The medium according to claim 1, wherein the polyvinyl alcohol has a critical micelle concentration of 0.1 to 5 mg/ml.

3. The medium according to claim 1, wherein the polyvinyl alcohol has a hydrolysis ratio of 60 to 95%.

4. The medium according to claim 2, wherein the polyvinyl alcohol has a hydrolysis ratio of 60 to 95%.

5. A method of preventing degradation of an albumin-containing medium, comprising:
adding polyvinyl alcohol to the medium,
wherein a weight ratio of the albumin in the medium to the polyvinyl alcohol added to the medium is 1:1.1 to 100, and
an amount of fatty acid binding to the albumin is not more than 2.2 mg per 1 g of the albumin.

6. A method of culturing an iPS cell, comprising:
culturing the iPS cell in the culture medium according to claim 1.

7. A method of culturing an iPS cell, comprising:
culturing the iPS cell in the culture medium according to claim 2.

8. A method of culturing an iPS cell, comprising:
culturing the iPS cell in the culture medium according to claim 3.

9. A cell culture, comprising an iPS cell in the culture medium according to claim 1.

10. The medium according to claim 1, wherein the albumin comprises recombinant human albumin.

11. The medium according to claim 1, wherein the albumin and the polyvinyl alcohol are included in the medium in the weight ratio of 1:1.1 to 15.

12. The method according to claim 5, wherein the albumin in the medium comprises recombinant human albumin.

13. The method according to claim 5, wherein the weight ratio of the albumin in the medium to the polyvinyl alcohol added to the medium is 1:1.1 to 15.

14. The medium according to claim 1, wherein the amount of fatty acid binding to the albumin is from 1 to 2 mg per 1 g of the albumin.

15. The method according to claim 5, wherein the amount of fatty acid binding to the albumin is from 1 to 2 mg per 1 g of the albumin.

* * * * *